United States Patent [19]

Englar et al.

[11] 4,447,395
[45] May 8, 1984

[54] SAMPLING DEVICE

[75] Inventors: Donald G. Englar, Frederick, Md.; Robert G. Altman, Mauldin, S.C.

[73] Assignee: The United States of America as represented by the Secretary of the Army, Washington, D.C.

[21] Appl. No.: 348,539

[22] Filed: Feb. 12, 1982

[51] Int. Cl.$^3$ .................... G01N 33/00; G01N 35/04
[52] U.S. Cl. .................................... 422/68; 422/63; 422/64; 422/100; 422/104; 436/46
[58] Field of Search .................... 422/63, 67, 64, 104, 422/68; 436/46

[56] References Cited

U.S. PATENT DOCUMENTS

| | | | |
|---|---|---|---|
| 2,879,141 | 3/1959 | Skeggs | 23/253 |
| 3,038,340 | 6/1962 | Isreeli | 73/423 |
| 3,081,158 | 3/1963 | Winter | 422/64 |
| 3,178,266 | 4/1965 | Anthon | 23/253 |
| 3,266,322 | 8/1966 | Negersmith et al. | 73/423 |
| 3,567,393 | 3/1971 | Welch | 422/64 |
| 3,592,605 | 7/1971 | Noma et al. | 422/64 |
| 3,594,129 | 7/1971 | Jones | 23/253 |
| 3,617,222 | 11/1971 | Matte | 422/64 |
| 3,804,593 | 4/1974 | Smythe et al. | 23/230 R |
| 4,000,973 | 1/1977 | Petersen | 23/230 R |
| 4,200,607 | 4/1980 | Suzuki | 422/64 |
| 4,224,032 | 9/1980 | Glover et al. | 436/46 |

Primary Examiner—Michael S. Marcus
Attorney, Agent, or Firm—Neil K. Nydegger; Arthur I. Spechler; Werten F. W. Bellamy

[57] ABSTRACT

Apparatus for processing and analyzing various liquids, such as blood serum, includes an indexable table for supporting a plurality of liquid sample containers. A probe is inserted into each sample container in succession. During probe insertion, a portion of the sample to be analyzed is withdrawn by the probe from the respective container and moved to a station where it can be analyzed and tested. The probe is then moved to a station where it can be washed prior to insertion into the next sample container. The drive mechanism for the apparatus is characterized by the fact that all indexing mechanisms and actuator cams are mounted on a single rotatable shaft and arranged such that each periodic function performed by the mechanism is directly coupled to the rotation of the shaft.

2 Claims, 3 Drawing Figures

SAMPLING DEVICE

The invention described herein may be manufactured, used, and licensed by or for the Government for governmental purposes without the payment to use of any royalty thereon.

BACKGROUND OF THE INVENTION

This invention relates generally to an indexing drive mechanism for a sampling device. More particularly, the invention relates to a device, for sequentially processing discrete samples, in which all operational functions of an indexing mechanism are activated by a single rotatable shaft. The present invention is particularly, though not exclusively, useful in the processing, testing and analyzing of liquid samples, such as blood, urine or water.

DESCRIPTION OF THE PRIOR ART

It has been proposed as an aid for the testing or analyzing of a plurality of discrete samples, that an indexing mechanism be employed which holds the samples, and sequentially presents them to a pick-up station where each sample can be withdrawn and further moved to a testing station. Specific tests and procedures for analyzing particular liquid samples to determine selected characteristics have been established by teachings well known in the art. Indexing mechanisms which allow sequential performance of these tests on a series of individual samples have, however, been primarily designed for use in a chemical or clinical laboratory environment and have been relatively complex in both construction and operation. Operational problems have also been encountered when, due to the independent operation of various parts of a sample supply device, there is a requirement to synchronize the device's movement. The problems inherent in these complexities become even more pronounced when operation outside a laboratory environment is considered.

Numerous situations can be envisioned in which a reliable, easily transportable and relatively maintenance-free sample supply device would be an operational necessity. For instance, use of a sample supply device by military personnel in a field environment could foreseeably include situations in which tactical mobility, adverse weather conditions, or the lack of electrical power could limit or preclude the usefulness of presently available devices. Accordingly, some of the objects of this invention are to reduce the impact of these problems by providng a rugged supply sample device of reduced complexity which is small and compact and adaptible for field use in military operations. The improved sampling device of the present invention substantially overcomes problems of bulk, and the inherent requirement for a fixed station operation, by employing a compact construction which allows for ease of mobility and reliable operation in a variety of environments with minimal maintenance requirements. These characteristics permit flexibility in the use of the device and adaptability to a wide range of uses.

SUMMARY OF THE INVENTION

A preferred embodiment of the novel sampling device includes a rotatable drive shaft, an indexing assembly, and a probe assembly. All operational aspects of the device result from the motion of the drive shaft. Drive means rotate the drive shaft, on which are mounted a plurality of disks and cams. The disks and cams cooperate with appropriate subassemblies to operate the indexing assembly and probe assembly.

The novel features of this invention, as well as the invention itself, both as to its organization and operation will be best understood from the accompanying drawings, taken in conjunction with the accompanying description, in which similar reference characters refer to similar parts, and in which:

DESCRIPTION OF THE PREFERRED EMBODIMENTS

Figure 1:
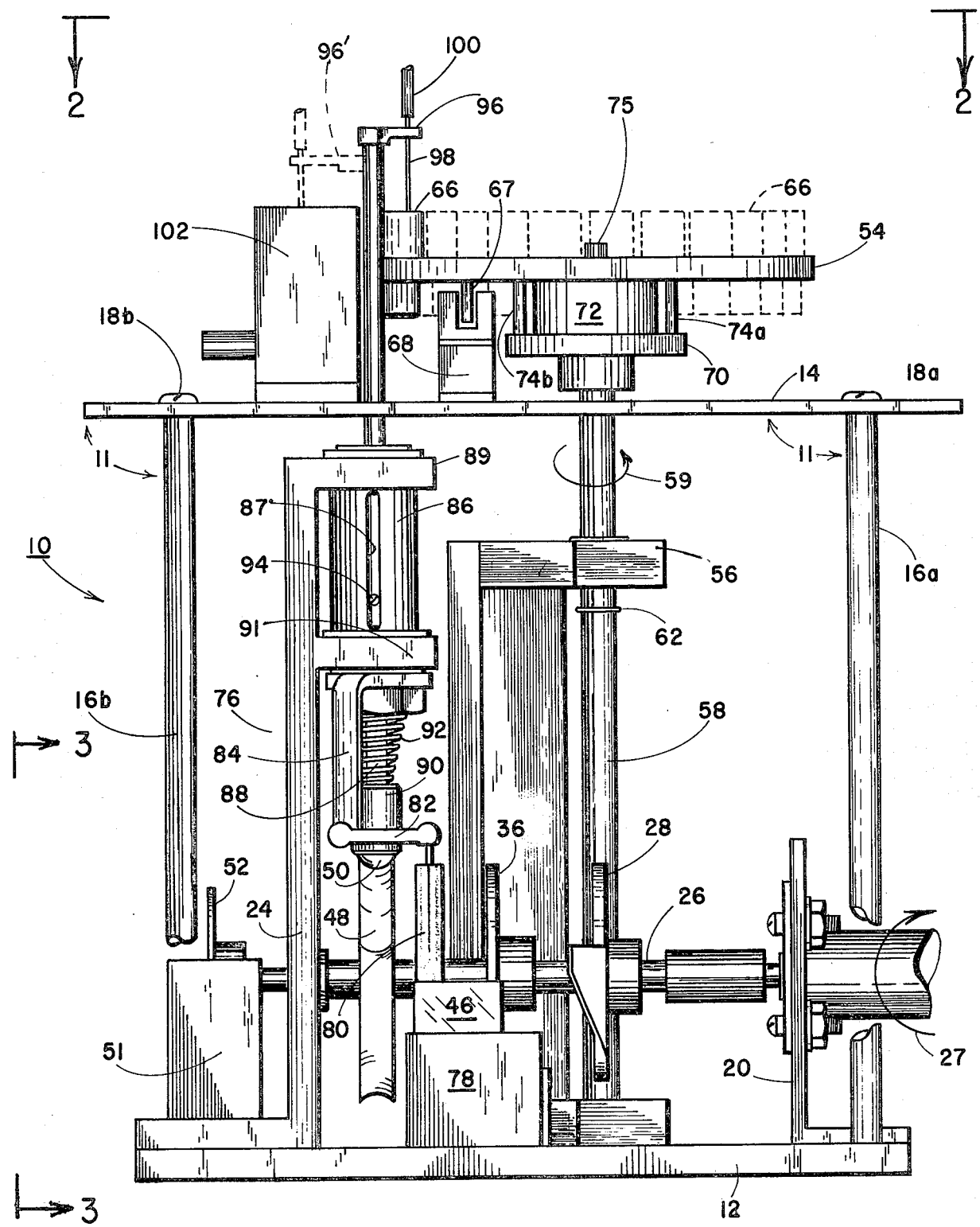
FIG. 1 is a front elevational view of the sampling device with portions broken away for the purpose of clarification.
Figure 2:
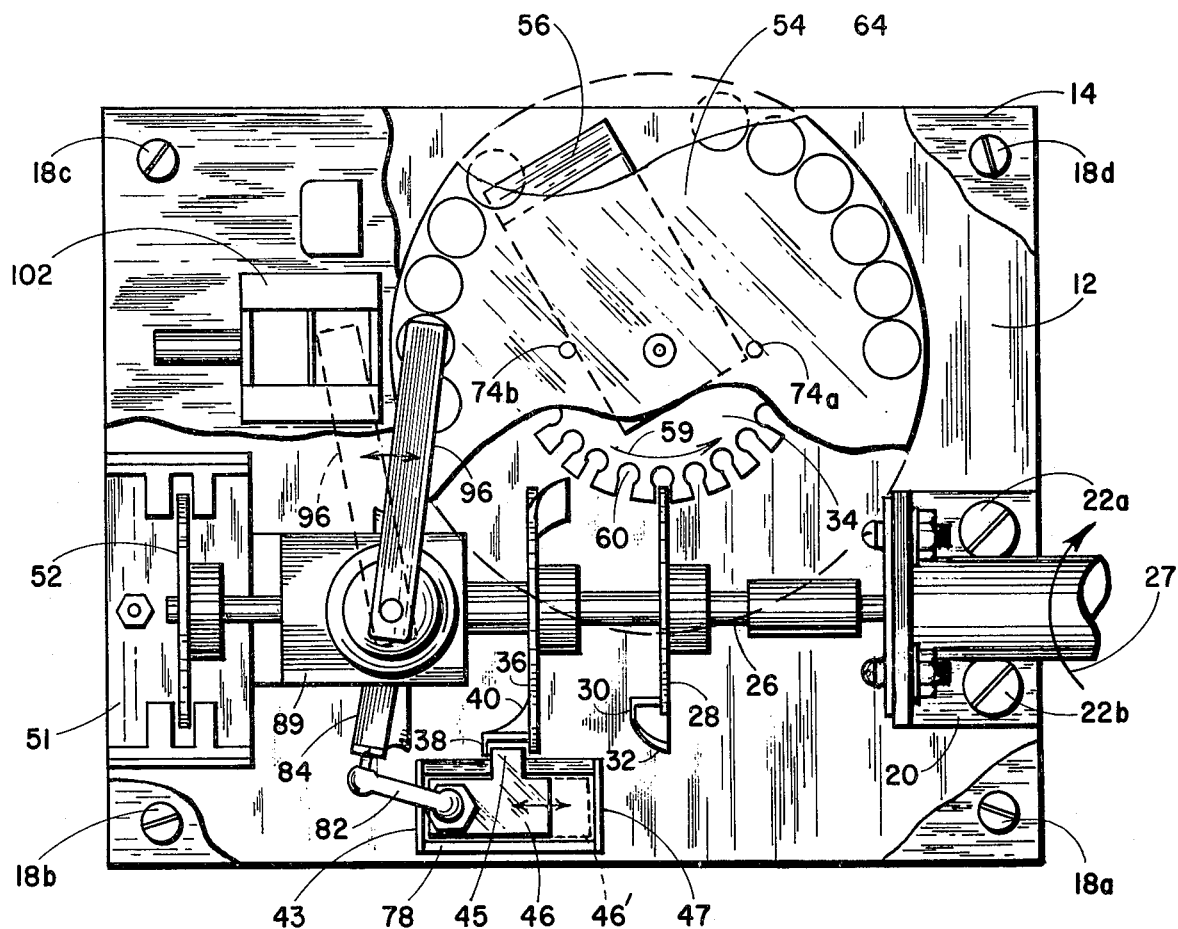
FIG. 2 is a plan view of the sampling device with portions broken away and illustrated in sections for the purposes of clarification and illustration.

Referring now to FIGS. 1 and 2, there is shown the sampling device 10 that obtains its structural rigidity from a frame assembly 11 which consists of a base plate 12, a top plate 14 and four rods 16a, 16b, 16c and 16d (16c and 16d not shown) whose respective ends are rigidly attached to the base 12 and the top plate 14 by any suitable means, such as screws 18a, 18b, 18c, and 18d (18c and 18d not shown).

A right angle bracket 20 is rigidly attached to the base 12, as shown in FIG. 1 and FIG. 2, by any suitable means, such as screws 22a and 22b. Also rigidly attached to base 12, by means such as screws, is a brace 24. A drive shaft 26 is journaled through the bracket 20 and the brace 24 for rotation about an axis generally parallel to the base 12. Rotation of shaft 26, in the direction indicated by arrow 27, can be accomplished by any appropriate means known in the art which would include, but is not limited to, hand operation or a motor drive. Fixedly mounted on shaft 26 by any suitable means, such as a set screw or splines, is a once per revolution indexing disk 28. As best shown in FIG. 2, the disk 28 is constructed, with a leading cam edge 30 and a cam drive portion 32 for the purpose of driving a Geneva gear plate 34 in a manner to be explained hereinafter. Also fixedly mounted on the shaft 26, by any suitable means, is a twice per revolution indexing disk 36. The disk 36, as shown in FIG. 2, is constructed with a leading cam edge 38 and a cam drive portion 40 which are diametrically opposite a second leading cam edge 42 and a second cam drive portion 44. This disk 36 is constructed to push against a tab 45, that is formed on a block 46. Disk 36 thereby drive the block 46 between alternate positions twice during one revolution of the shaft 26 for a purpose which will be discussed below.

Fixedly attached to the drived shift 26, by any suitable means, is a double lobed cam 48. The cam 48 urges against a roller bearing 50 in a manner which causes the bearing 50 to cyclically translate up and down twice for each revolution of the shaft 26. Also fixedly mounted on the shaft 26 is an interrupter disk 52. A hole 53, as shown in FIG. 3, formed in the disk 52 may be positioned relative to the shaft 26 such that during any desired portion of a revolution of the shaft 26 a photo electric circuit (not shown), held in a housing 51, can be completed in a manner well known in the pertinent art, for any purpose desired by the operator of the apparatus 10.

Figure 3:
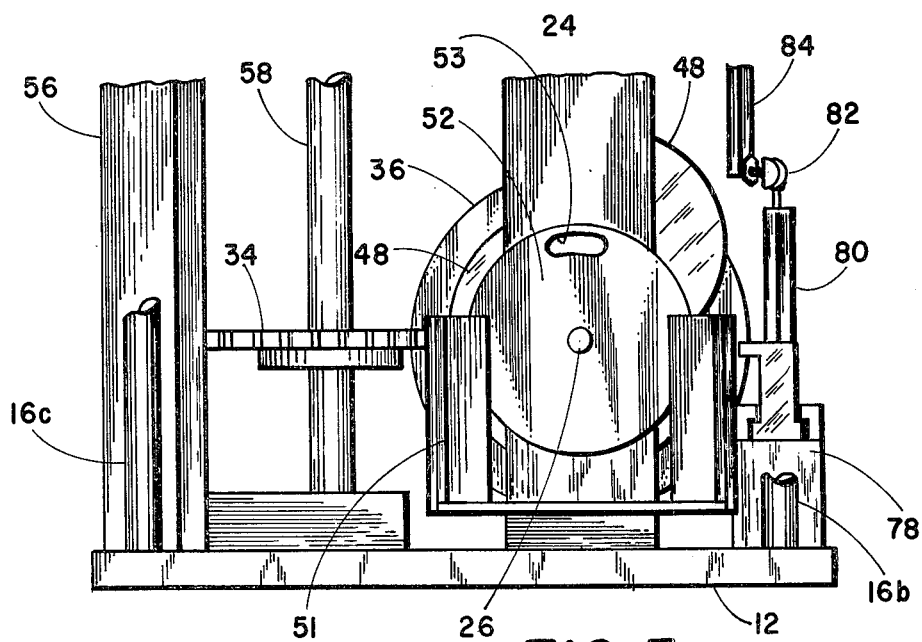
FIG. 3 is a partial side elevational view on the line 3—3 of FIG. 1.

Turning now to a description of the mechanism for the rotation of a sample holding tray 54, it can be seen in FIG. 1 and FIG. 3 that one side of a U-shaped support 56 is rigidly attached to the base 12 by any suitable means. A support shaft 58 is journaled against the attached side of support 56 and journaled through the free side of the support 56. As held by support 56, the support shaft 58 is mounted for rotation in the direction of the arrow 59, about an axis generally perpendicular to the base 12. The Geneva gear plate 34, including notches 60 formed therein, as shown in FIG. 2, is secured to the support shaft 58. A retainer ring 62 is formed on the support shaft 58 to prevent its slippage out of the support 56.

The sample support tray 54 is removably secured to the upper end of support shaft 58 in a manner to be described below. The sample holder tray 54 is generally circular and incorporates adjacent to the periphery thereof, as shown in FIG. 2, a generally circular array of cup mounting holes 64. Samples cups 66 are removably positioned within these holes 64 by insertion therewithin. At the center of the tray 54 is a hole (not shown) through which a narrow portion 75 of the shaft 58 is inserted. On the underside of the tray 54 is a tang 67 which is used to cooperate with a light source (not shown) and a photo electric cell (not shown) which are mounted in a housing 68 and function in a manner well known in the art to activate a suitable means for insuring the sample tray is correctly oriented and, when desired, for ceasing operation of the apparatus 10 after one complete revolution of the sample tray 54. Interaction of the tang 67 with the photocell in housing 68 can be made to interrupt circuitry connected with the photocell and thereby function as a means for counting revolutions of the tray 54. Attachment of the sample tray 54 to the support shaft 58 can be accomplished by the following means, as shown in FIG. 1. A support plate 70 is fixedly attached to shaft 58 by any suitable means, such as a set screw. Fixedly attached to the support plate 70 is a spacer 72 and two, or more, retainer pins 74a and 74b. The length of the retainer pins 74a and 74b exceed the height of spacer 72 by not more than the depth of recesses (not shown) on the underside of sample tray 54. With this configuration, the tray 54 can be placed on the apparatus 10 in a way so as to rest on spacer 72 while a narrowed portion 75 of the shaft 58 protrudes through a hole formed in the center of the tray 58 and the retainer pins 74a and 74b are inserted into the recesses on the underside of tray 54.

A probe assembly 76 is constructed as follows: A base block 78 is rigidly attached to the base plate 12 by any suitable means, such as glue or welding. The block 46 is slidably mounted on base block 78 in a manner to operatively cooperate with the indexing disk 36, as is shown in FIG. 2. A post 80 is rigidly attached to block 46 as shown in FIG. 1 and FIG. 3, by any suitable means, such as welding. A link 82 is attached to the post 80 by a suitable means such as a ball and socket connection. A similar connection is used to attach the other end of link 82 to a swingable arm 84. The swingable arm 84 is rigidly secured to a sleeve 86 which includes a longitudinal slot 87 formed therein, as shown in FIG. 1. Also, as shown in FIG. 1, the sleeve 86 is journaled through a horizontal extension 89 and 91 of the brace 24 for rotation about a vertical axis.

Included in the probe assembly is a follower arm 88 which passes through the sleeve 86 and is journaled through the horizontal extensions 89 and 91 of the brace 24 for rotation about a vertical axis. The roller bearing 50 is held at the lower end of the follower arm 88 by a grip socket 90 that is rigidly attached to the follower arm 88. This grip socket is constructed to allow for rotation of the roller bearing 50 and to also provide a stop for a spring 92. The spring 92 is placed around the follower arm 88 and positioned between grip socket 90 and the brace 24, as shown in FIG. 1, so that while the follower arm 88 may translate up and down the roller bearing 50 is continuously urged against the double lobed cam 48. A pin 94 is rigidly attached to the follower arm 88 and placed for travel within the slot 87 of the sleeve 86. This arrangement allows the follower arm 88 to translate in accordance with the urging of cam 48 and to simultaneously rotate in accordance with the rotation of the sleeve 86.

Fixedly attached to the upper end of follower arm 88, as shown in FIG. 1, is a probe arm 96. A take off device 98, such as a hollow needle and a tube 100, or any other suitable sampling mechanism, can be removably attached to the probe arm 96. During the operation, a sample can be removed (as by suction) from a sample cup 66 by the take off device 98 and passed to a work station by any suitable means, such as the tube 100. The take off device 98 can then be moved to a wash station 102 before returing to another sample cup 66 for sample retrieval. Also, it is noted that this apparatus 10 can be employed to place samples on the tray 54 rather than to remove them from the tray 54. The possibilities of such operation would include, but need not be limited to, the dispensing of measured amounts of medicines or the addition of ingredients to previously measured samples.

A counter 110 can be rigidly mounted, by any suitable means, to the top plate 14, as shown in FIG. 2. Operatively associated with the counter 110 are a switch 112 and a depressor arm 114, as is best shown in FIG. 2. The switch 112 is mounted on the counter 110. One end of the depressor arm 114 is swingably attached to counter 110 while the other end is urged into the path of the sample cups 66 in such a way that each sample cup during rotation of tray 54 sequentially causes the depressor arm 114 to swing against and engage switch 112. As each respective sample cup 66 passes beyond the point in its path where it causes the depressor arm 114 to engage switch 112, the depressor arm 114 is urged to swing away from and thereby release switch 112. Depressor arm 114 is then urged into the path of the sample cups 66 where it can press against the next sample cup for repetition of the operation. In this manner, the switch 112 can be alternately engage and released to activate counter 110 for various purposes, such as a start-stop function for the apparatus 10.

Overall operation of the present invention is best described by considering the interaction of each subassembly with the rotation of the drive shaft 26. As seen in FIG. 1 and FIG 2, each revolution of the shaft 26 results in a corresponding revolution of the one per revolution indexing disk 28, the twice per revolution indexing disk 36, the double lobed cam 48 and the interrupter disk 52.

First, as best shown in FIG. 1, consideration is given to the mechanism for moving the sample holder tray 54 in a manner that will sequentially present a sample holder cup 66 into the position where it will be aligned with the probe take off device 98. As best shown in FIG. 2, this operation is governed by rotation of the once per revolution indexing disk 28. The configuration of the once per revolution indexing disk 28 in such that every complete revolution thereof will function to advance the Geneva gear plate 34, in the direction of the arrow 59. More specifically, during most of the revolution of the once per revolution indexing disk 28, its peripheral edge rides in a notch 60 of the Geneva gear plate 34 and thus holds plate 34 stationary. At one point in the revolution of disk 28, however, the leading cam edge 30 enters the next succeeding notch 60 on plate 34 while, simultaneously, the peripheral edge of disk 28 disengages from the notch in which it has been riding. The driving cam portion 32 then urges rotation of plate 34 in the direction of arrow 59 until the preipheral edge of disk 28 enters the notch to hold the plate 34 stationary in its new position. The Geneva gear plate 34 remains stationary in this new position until the leading cam edge 30 of the driving cam portion 32 of the disk 28 enters the next succeeding notch 60 to repeat the driving process. There is one notch 60 formed in the preiphery of Geneva gear plate 34 for each of the array of sample cup mounting holes 64 formed on the sample holder tray 54. From this arrangement it will be understood that each revolution of the one per revolution indexing disk 28 will function to advance the sample holder ;tray 54 one sample cup position to, in turn, index a new sample cup 66 into alignment with the probe take off device 98.

Next, it can be recognized that operation of the probe arm 96 requires horizontal and vertical movements which are respectively caused by the driving actions of the twice per revolutions indexing disk 36 and the double lobed cam 48. Considering first the horizontal motion of the probe arm 96, it will be understood that during one complete revolution of the drive shaft 26 the probe arm 96 will be reciprocated between the position shown in FIG. 2 and a second position indicated by identifying character 96' in FIG. 2. Accomplishing this motion begins with rotation of the drive shaft 26. This rotation, in turn, rotates the twice per revolutions indexing disk 36 and, as shown in FIG. 2, the drive portion 40 of disk 36 contacts tab 45, driving block 46 to a position indicated by identifying character 46'. After block 46 has been driven to position 46' the indexing disk 36 continues to urges against tab 45 and thus holds block 36 stationary against a lip 47. As indexing disk 46 continues to rotate, drive portion 44 comes in contact with the tab 45 and drives the block 46 back to its start position, as shown in FIGS. 1 and 2. The disk 36 is then urged against the tab 45 to hold the block 46 stationary in place against a second lip 43 until the drive drive portion 40 again makes contact with tab 45 to repeat the cycle.

The reciprocal translational motion of the block 46 is transmitted by the post 80 through the link 82 and the swingable arm 84 into a correspondingly reciprocal rotational motion of the sleeve 86. As best seen in FIG. 1 this rotational motion is directly transferred from the sleeve 86 through the pin 94, and hence through follower arm 88 into a cyclical swinging motion of probe arm 96. In this manner the probe arm 96 can be alternately positioned above a sample cup 66 and the wash station 102.

During the swing motion of the probe arm 96, as described above, it is necessary that the take off device 98 clear the edge of a sample cup 66 and the edge of wash station 102. Thus the probe must be in an elevated position to accomplish the required clearance. The take off device 98, however, must be lowered into a sample cup 66 for sample retrieval and lowered into the wash station 102 for cleaning. Therefore, appropriate vertical reciprocation of the take off device 98 into and out of the sample cup 66 and the wash station 102 must be coordinated with the horizontal swinging action of the probe arm 96.

The vertical motion of the take off device 98, which is detachably secured to the probe arm 96, begins with the rotation of the drive shaft 26 and the resultant rotation of the double lobed cam 48. The lobes of cam 48 are positioned relative to the drive shaft 26 such that during periods when the probe arm 96 is not being swung horizontally the probe arm 96 is lowered and raised due to the action of the cam 48. In operation, the roller bearing 50 is urged against the double lobed cam 48 by the spring 92. Thus, as the cam 48 is rotated, the roller bearing 50 and the attached follower arm 88 will reciprocate vertically in accordance with the shape of cam 48. In this manner, the probe arm 96 and take off device 98, which are operatively connected to the follower arm 88, are made to move into and out of either the sample cup 66 or the wash station 102.

Coordination of the aforementioned motions is accomplished by appropriate alignment of the once per revolution indexing disk 28, the twice per revolution indexing disk 36, and the double lobed cam 48, on the drive shaft 26. When properly aligned the probe 96 is made to lower into a sample cup 66, retrieve a sample through activation of the take off device 98 by any suitable means, as by suction, and then withdraw from the sample cup 66. The probe arm 96 is then in the evelvated position and is swung to a position above the wash station 102. The probe arm 96 and device 98 are then lowered into the wash station 102 while simultaneously the sample holder tray 54 is advanced to position a new sample cup in alignment for action with the probe arm 96. The probe arm 96 is then withdrawn from wash station 102, and once in the elevated position, it is horizonally swung to position the take off device 98 above the sample cup 66. The probe arm 96 and take off device 98 are then lowered into the sample cup 66 and the cycle is repeated.

Depending upon the desires of the operator, the apparatus 10 may be operated manually, as by rotating the drive shaft 26 with a crank handle (not shown). Additionally, revolutions of the drive shaft 26 can be counted or the apparatus 10 can be stopped after one rotation of the drive shaft 26 by the action of the interrupter disk 52 on the photo electric cell and associated circuitry (not shown) that is held in housing 51. Another function of the interrupter disk 52, when activating the photo cell held in housing 51, is to verify correct orientation or synchronization of the apparatus 10 for the sampling operation. Also, as previously mentioned, the operation of apparatus 10 can be stopped after one complete revolution of the sample holder tray 54 through activation of the photo electric circuitry (not shown) by the tang 67 as it cooperates with a light source and the photo electric cell which are held in housing 68. In addition to, or instead of, stopping operation of the apparauts 10, the tang 67 and the interrupter disk 52 can be used in cooperation with the respective photoelectric cells to activate the respective photo electric circuit for other purposes, such as activation of the take off device for counting the number of operations performed by the apparatus 10. It should also be recognized that replacing the once per revolution indexing disk 28 and the twice per revolution indexing disk 36 with respective disks having reverse slope driving cam portions will allow apparatus 10 to be operated for sequencing sample cups 66 on tray 54 in the reverse direction. In this mode of operation, rotation of drive shaft 26, counter to arrow 27, will cause rotation of tray 54 in a direction counter to arrow 59 while also providing for the proper horizontal motion of probe 96.

We claims:

1. Apparatus that is easily transportable and adapted for field use in military operations, said apparatus comprising:

a base, a tray for holding samples, a probe arm, a drive shaft, means for mounting said drive shaft for rotation on said base, means connecting said drive shaft with said probe arm relative to said tray for cooperating with at least a portion of said samples and for reciprocating said probe arm along a path transverse to said tray and for swinging said probe arm transversely to said path during one revolution of said drive shaft, means connecting said drive shaft with said tray for indexing said tray to place said samples in a position for cooperation with said probe arm comprising a support shaft disposed transversely to said base and having one end removably attached to said tray and the other end mounted on said base for rotation with respect thereto, a Geneva gear rigidly attached to said support shaft, and a first indexing disk rigidly attached to said drive shaft and operatively associated with said Geneva gear for sequentially rotating said support shaft, said means connecting said drive shaft with said probe arm for swinging said probe arm comprises:

a second indexing disk rigidly attached to said drive shaft, a block slidably mounted on said base and operatively associated with said second indexing disk for recriprocal translation of said block between a first position and a second position, a follower arm attached to said probe arm, a brace rigidly mounted on said base for supporting said follower arm, a pin fixed on said follower arm, a sleeve formed with a slot and slidably disposed on said follower arm with said pin seated in said slot for simultaneously allowing independent translation of said follower arm inside said sleeve and concurrent rotation of said follower arm with said sleeve, and means operatively connecting said block with said sleeve for transmitting the reciprocal translation of said block into rotation of said sleeve whereby said probe arm reciprocally swings toward and away from said samples.

2. Apparatus adapted for military field use and easily portable comprising:

a base, a tray for holding samples, a probe arm for cooperating with at least a portion of said samples on said tray, a drive shaft rotatably mounted on said base, a support shaft disposed transversely to said base and having one end removably attached to said tray and the other end mounted on said base for rotation with respect thereto, a Geneva gear rigidly attached to said support shaft, a first indexing disk rigidly attached to said drive shaft and operatively associated with the Geneva gear for sequentially rotating said support shaft, a double lobed cam rigidly attached to said drive shaft, a follower arm having a first end rigidly attached to said probe arm and a second end which urges against and rides on said double lobed cam for alternately raising and lowering said probe, a brace rigidly mounted on said base for supporting said follower arm, a second indexing disk rigidly attached to said drive shaft, a block slidably mounted on said base and operatively associated with said second indexing disk for reciprocal translation of said block between a first position and a second position, a pin fixed on said follower arm, a sleeve formed with a slot and slidably disposed on said follower arm with said pin seated in said slot for simultaneously allowing independent translation of said follower arm inside said sleeve and concurrent rotation of said follower arm with said sleeve, means operatively connecting said block with said sleeve for transmitting the reciprocal translation of said block into rotation of said sleeve whereby said probe arm swings between an aligned position where said probe arm cooperates with samples on said tray and a nonaligned position, and means for rotating said drive shaft.

* * * * *